United States Patent [19]

Ho

[11] Patent Number: 4,488,556
[45] Date of Patent: Dec. 18, 1984

[54] AC MODE OPERATION OF CHEMFET DEVICES

[75] Inventor: Nelson Ho, West Valley, Utah

[73] Assignee: Critikon, Inc., Tampa, Fla.

[21] Appl. No.: 384,710

[22] Filed: Jun. 3, 1982

[51] Int. Cl.³ ............................................ G01N 27/30
[52] U.S. Cl. .................................. 128/635; 204/406; 204/416; 357/25
[58] Field of Search ................... 204/406, 416; 357/25; 324/71.5, 71.6; 128/635

[56] References Cited

U.S. PATENT DOCUMENTS

| | | | |
|---|---|---|---|
| 4,020,830 | 5/1977 | Johnson et al. | 128/635 |
| 4,385,274 | 5/1983 | Shimada et al. | 204/416 X |

OTHER PUBLICATIONS

Steven L. Garverick et al., IEEE Trans. on Electron Devices, vol. ED-29, No. 1, pp. 90-94, Jan. 1982.

Primary Examiner—G. L. Kaplan
Attorney, Agent, or Firm—Audley A. Ciamporcero

[57] ABSTRACT

A chemically sensitive field effect device has its chemically selective system exposed to the material being investigated. The device is driven by a time varying, typically sinusoidal, current source. A protected reference electrode is also in contact with the body under investigation, and is biased at a predetermined DC level relative to the chemically sensitive field effect device.

8 Claims, 6 Drawing Figures

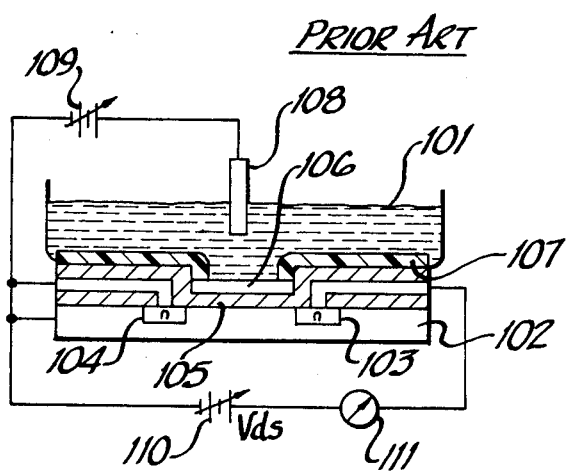
FIG-1  PRIOR ART
FIG-2  PRIOR ART
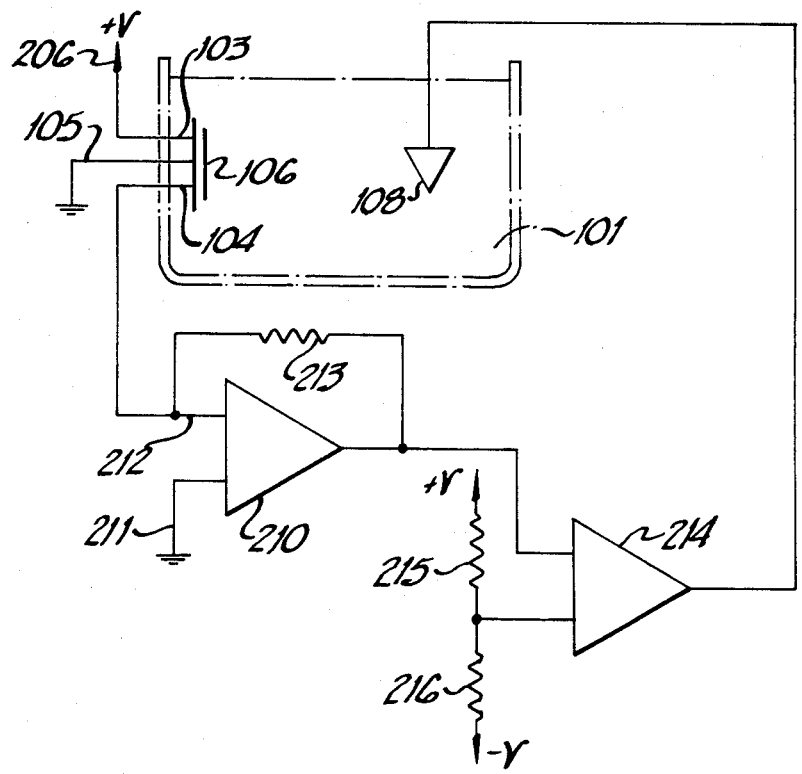

AC MODE OPERATION OF CHEMFET DEVICES

FIELD OF THE INVENTION

This invention relates to chemically selective sensors, and more particularly to chemically selective field effect devices popularly known as "Chemfets".

BACKGROUND OF THE INVENTION

The field of electrochemical sensors is one which occupies continuing research and commercial interest, for both industrial and medical applications. One class of sensor which shows considerable promise is the sort disclosed in U.S. Pat. No. 4,020,830 to Johnson et al. entitled "SELECTIVE CHEMICAL SENSITIVE FET TRANSDUCERS". The Johnson et al. patent describes a field effect device wherein a variably conductive channel extends between respective drain and source regions, with the drain to source current being modulated by a chemically selective system which overlays the channel region. In particular, the chemically selective system often includes an insulator layer, overlayed by a chemically selective membrane which reacts selectively to the ambient substance to be monitored. A reference electrode, suitably biased relative to the device, is coupled to the monitored material to facilitate selective interaction of the material to be monitored with the membrane system, thereby in turn modulating the drain to source current.

It has become popular in the art to classify chemically sensitive devices of the sort disclosed in the Johnson et al. patent by the nature of the chemically selective system, and the ambient materials with which they react. For example those reacting with ions are often designated "ISFETS", those reacting on an immunological basis are "IMFETS", and so on. As utilized herein, the term "chemfet" shall designate devices of the sort described, irrespective of the nature of the reaction between the chemically selective system of the device, and the designated ambient material. Likewise, the "chemfet" designation shall be utilized for such devices whether or not they utilize separate insulator and membrane overlayments, or simple insulator areas which acquire an oxidation layer or the like while in use, or a variety of other chemically selective systems. Further, the term shall designate unspecified applicable semiconductor devices, such as field effective devices, Schottky devices, and so on.

A common prior approach to utilization of chemfet devices is to maintain the device substrate at ground potential, to maintain the drain region at a specified DC potential, and to maintain the source electrode at some fixed potential relative to the drain, e.g., ground potential or virtual ground through an operational amplifier system. The reference electrode is maintained at a specified potential relative to the device (e.g., relative to the source electrode). Typically, such a configuration (i.e. "DC mode operation") operates for known devices at potentials in the range of 2 volts, DC reference electrode current in the range of 100 picoamps, and drain to source currents in the order of 100 to 500 microamperes.

Such operating constraints afford no difficulty for industrial or even in vitro medical applications, but provide potential problems for in vivo medical applications. For example, it is contemplated that chemfet devices may be utilized as the active element of an invasive intravenous or tissue catheter-type sensor, wherein the device directly serves to measure physiological parameters such as blood ion concentrations, blood gas tension, or the presence of immunological agents in the body. Generally, the chemfet device utilized in such application will be enclosed by a highly insulating, hermetically sealing material, except that the gate membrane area which overlies the drain to source conductive channel will be open to the ambient materials. In the event that the encapsulation should fail, or that there should occur a breach of the insulator/membrane system, there is an immediate and substantial risk of harm to the patient. In particular, such a fault would expose the patient to DC currents of 10 to 100 times the levels normally considered safe. Further, since the body of the patient would thereby become a portion of the circuit, conventional current monitoring techniques would be difficult to apply, and would in any event be subject to uncertainty regarding the actual path of the currents so generated.

It is, accordingly, an object of the present invention to provide safer modes of operation for chemfet devices, particularly addressing safety problems associated with direct in vivo applications of the devices. It is an associated object to provide such systems and apparatus which are essentially intrinsically safe by virtue of their operation, and which do not require current or voltage sensing followed by open or closed loop corrections and/or alarms.

SUMMARY OF THE INVENTION

The principles of the present invention are premised on the proposition that the human body has an inherent higher tolerance for alternating current than for direct current. Accordingly, in accordance with the principles of the present invention, a chemfet device has its drain to source circuit driven by continuously time varying, rather than Dc currents.

In a preferred embodiment, a chemfet-style device has its gate membrane area coupled to a substance to be monitored, for example the blood of a patient. A reference electrode also is coupled appropriately to the patient. The device has its drain connected to an AC source providing current in the range 10 Hz to 1 MHz, at rms current levels in the range 1 to 100 microamperes. The substrate is maintained at fixed potential (e.g., ground) and the source is coupled to a current to voltage converter. The output of such converter is utilized, through a comparator, to maintain the reference electrode at a fixed voltage relative to the device. Preferably, a large resistance couples the comparator to the reference electrode, and thereby limits the DC current exposure of the patient through the reference electrode.

DESCRIPTION OF THE DRAWINGS

FIG. 1 shows a chemfet device as disclosed in U.S. Pat. No. 4,020,830 to Johnson et al.

FIG. 2 shows a circuit schematic for utilization of chemfet-style devices in the DC mode common to the prior art.

BEST MODE FOR CARRYING OUT THE INVENTION

Figure 3:
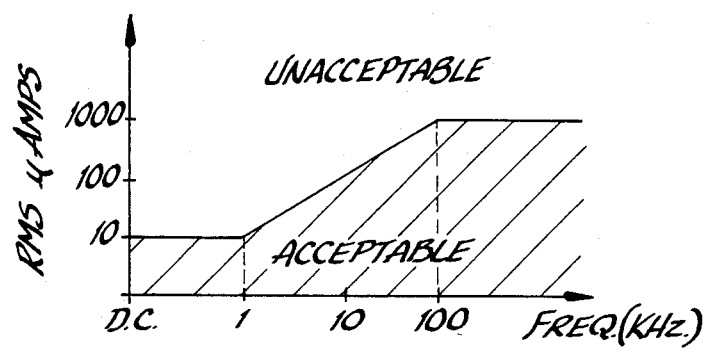
FIG. 3 shows a current vs. frequency plot, indicating coordinate areas which are respectively acceptable and unacceptable for in vivo applications.

Referring first to FIG. 1, there is shown for illustrative purposes a chemfet-style device, in particular one such as is disclosed in the previously cited Johnson et al. patent. The device substrate 102 carries respective drain and source regions 103 and 104, with the conductive channel disposed therebetween. An insulating layer 105 covers at least the conductive channel region between source and drain, and a chemiclly selective system 106, typically a selectively reactive membrane, is disposed immediately thereabove. A hermetic seal 107 insures that only the membrane system 106 is exposed to the ambient substance 101 to be measured. A reference electrode 108, also coupled to the ambient substance, is biased by a dc source 109 at a predetermined potential above that of the substrate 102 and source 104. A dc supply 110 biases the drain to source circuit, and a meter 111 monitors the drain to source current, which is known in the art to be a function of the conductive characteristics of the channel as modulated by the reaction of the membrane 106 with the ambient substance 101.

A more detailed version of this so-called "dc mode" operation of chemfet devices is shown symbolically in FIG. 2. In particular, the dc source 206 maintains the drain electrode 103 at a predetermined potential, with the substrate 105 being connected to ground and the source electrode 104 being maintained at virtual ground through connection to the current to voltage converter defined by operational amplifier system 210. In particular, the amplifier 210 with its associated feedback circuitry (shown symbolically simply as resistor 213, more complex circuitry may be employed as is known in the art) produces an output voltage which is proportional to the drain to source current of the device 106. That voltage is coupled to one input of a comparator 214, the other input of which is maintained at a predetermined reference potential established by resistive divider 215 and 216. Thus, the comparator 214 provides a corrected and hence stable potential to the reference electrode 108.

The substance to be monitored 101, shown in the drawings symbolically as a container of fluid or the like, may in fact be the body of a patient. The device 106 itself may be coupled directly to the patient, for example being located at the tip of a catheter inserted into the venous system of the patient. It will be evident, therefore, that if the device 106 suffers an electrical fault, either in the hermetic encapsulation of the device (107 in FIG. 1) or across the channel-membrane system (105 and 106 in FIG. 1), there will be potential for harm. Breach of isolation conditions supplying reference voltage to the reference electrode 108, whereby excessive current is provided, will similarly subject the patient to risk. The principles of the present invention are addressed to alleviation of this risk. In particular, the principles of the present invention essentially provide time variant or ac current to the drain to source circuitry of the device, and provide substantial dc protection for the reference electrode.

Referring next to FIG. 3, there is shown a depiction of levels of patient exposure to electrical current, as a function of signal frequency, which are presently believed realistic. The depiction set forth in FIG. 3 embodies standards promulgated by the American National Standards Institute (ANSI).

Figure 4:
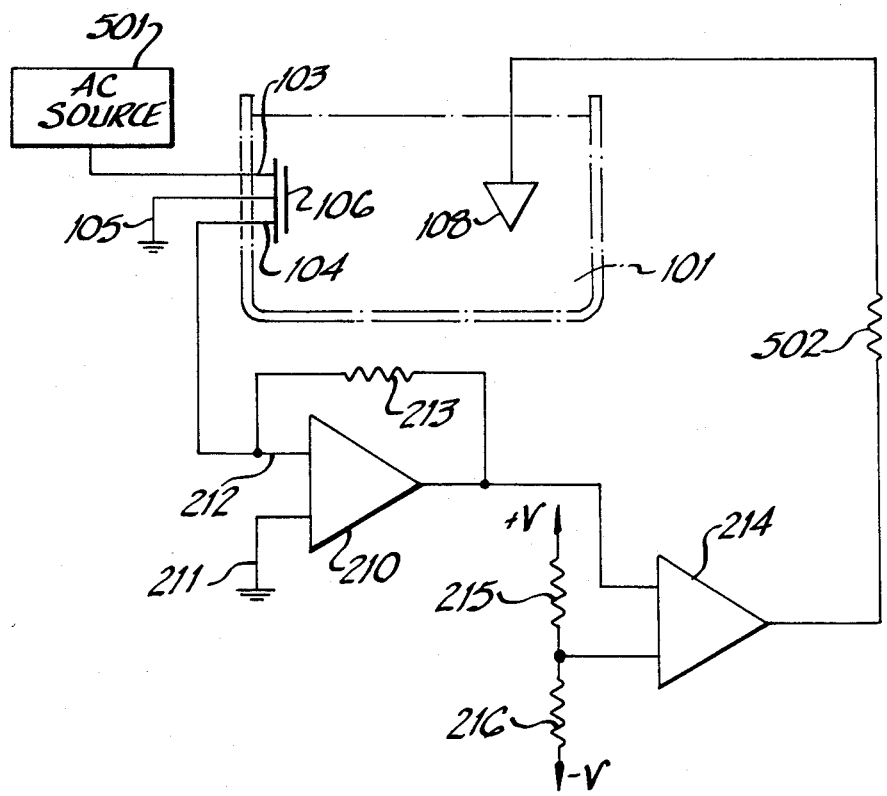
FIG. 4 shows a preferred embodiment of the principles of the present invention.

Referring next to FIG. 4, there is shown a preferred embodiment of the principles of the present invention, which in essence provides exemplary, stable chemfet operation which, within constraints and risks thereby entailed, also comports well with the standards set forth in FIG. 3. In FIG. 4, the drain to source current is supplied from an ac source 501, rather than the dc source 206 set forth in FIG. 2. The embodiment of FIG. 4 nevertheless relies on a current to voltage converter which couples a dc biasing/control voltage to the reference electrode 108 via a comparator 214, the other input of which is preset by a voltage divider 215 and 216. In the embodiment of FIG. 4, the reference electrode 108 is, as in the previous case, dc biased; the embodiment of FIG. 4 further provides, as a protective measure, a large resistance 502 which vastly reduces the potential dc current risk to the patient 101 via the reference electrode 108. In the embodiment of FIG. 4, the ac source provides substantially sinusoidal current in the amplitude range of 0.4 volts peak to peak, with a frequency in the range up to about 1 MHz. It will be noted that the device frequency response begins to roll off in the 200–500 kHz range. For such a system, the reference electrode is typically maintained at potentials in the range of $\pm 1$ volt. In such a system, drain to source currents are typically in the area of a few hundred microamperes rms.

The embodiment of FIG. 4 shows a grounded connection for the substrate 105; it will be appreciated that fixed or adaptive substrate potentials other than ground may be employed as well, depending upon the needs or requirements of the designer.

Figure 5A:
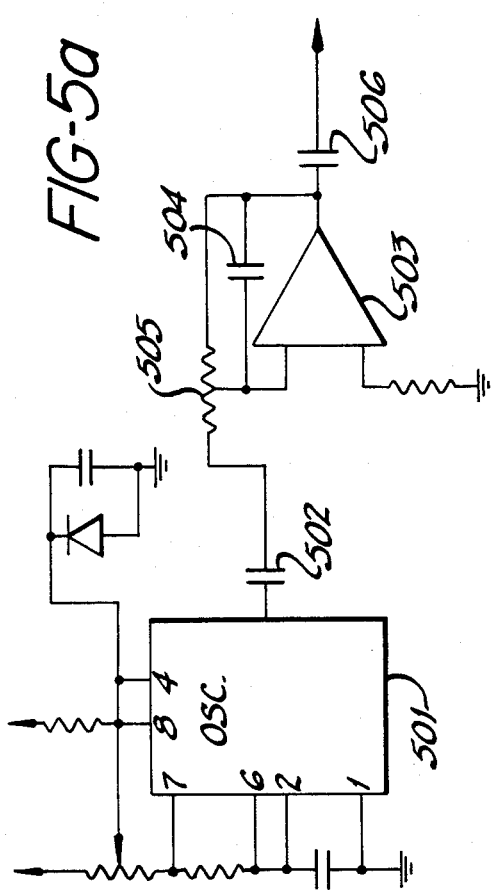
FIGS. 5a and 5b show illustrative circuits for preferred implementation of the embodiment of FIG. 4.
Figure 5B:
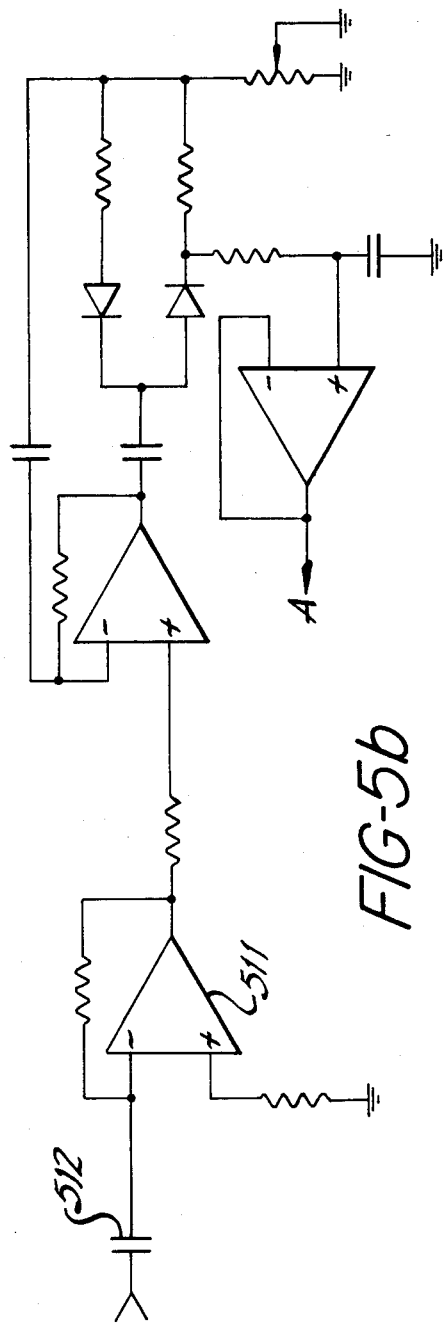

Referring next to FIGS. 5A and 5B, there are shown, respectively, illustrative circuits for the embodiment of FIG. 4. In particular, the embodiment of FIG. 5A represents an illustrative ac source, whereas the circuitry of FIG. 5B sets forth an illustrative current to voltage converter such as the amplifier system 210 of FIG. 4. In fact, the circuitry of FIGS. 5A and 5B is of quite common pedigree, representing one of many ways to embody the circuitry more generally shown in FIG. 4. The circuitry of FIGS. 5A and 5B is, however, presented for completeness of disclosure, so that those of ordinary skill in the art could not possibly fail to make and use the present invention without extensive experimentation.

In FIG. 5A, an oscillator 501, based on a commercially available model 555 timer, via coupling capacitor 502 produces a time variant waveform which is amplified and shaped at amplifier 503. In particular, feedback capacitor 504 smooths the corners of the waveform, and resistive tap 505 adjusts the amplitude. A further coupling capacitor 506 eliminates dc components as the waveform is coupled to the drain electrode of the chemfet device.

FIG. 5B shows an exemplary embodiment of the amplifier 210 schematic of FIG. 4. In FIG. 5B, the time variant waveform from the source electrode of the chemfet device is delivered through a dc-eliminating coupling capacitor 512 to a high frequency amplifier 511. The balance of the FIG. 5B circuitry constitutes a handbook style ac to dc converter, producing at output terminal "A" a dc voltage for coupling to the comparator 214 of FIG. 4.

In summary, the principles of the present invention relate to operation of a chemfet device in an ac mode. As used herein, the term "ac" is meant in its broadest possible connotation, that is, time variant, which may be sinusoidal, or periodic, or aperiodic. It will be appreciated that the embodiments set forth herein have at times been broadly schematic and even symbolic, and that the more detailed circuitry set forth has been proferred for illustrative purposes only. Numerous alternative embodiments will occur to those of ordinary skill in the art without departure from the spirit or the scope of the principles of the present invention.

I claim:

1. In combination, a chemically sensitive field effect transducer apparatus, means for coupling a sinusoidal drain-source potential to said transducer, and means for maintaining the gate of said transducer at a DC potential equal to the combination of a bias potential plus an electrochemically generated potential by a substance being sensed.

2. Apparatus as described in claim 1 and further comprising a reference electrode maintained at a predetermined DC bias relatve to the source electrode.

3. Apparatus as described in claim 2 wherein said means for generating generates a waveform having a frequency in the range between 10 Hz. and 1 MHz.

4. Apparatus as described in claim 3 wherein said means for generating generates a waveform having a frequency in the range between 100 kHz. and 200 kHz.

5. Apparatus for sensing the presence of a specified substance in a subject comprising:

(a) a chemically sensitive field effect device having respective drain and source connections, a drain to source conduction path, and a chemically selective system overlying said path and modulating current therein in response to presence of said substance in said subject;

(b) a reference electrode coupled to said subject;

(c) means for generating and for coupling to said conduction path a sinusoidal time variant signal; and (d) means, coupled between said source and said reference electrode, for establishing a gate potential consisting of a bias potential plus the potential generated electrochemically by said specified substance.

6. Apparatus as described in claim 5 wherein said means for generating comprises means for generating a substantially sinusoidal current waveform having a mean value of approximately zero volts.

7. Apparatus as described in claim 6 wherein said means for generating generates a waveform having a frequency in the range between 10 Hz. and 1 MHz.

8. Apparatus as described in claim 6 wherein said means for generating generates a waveform having a frequency in the range between 100 kHz. and 200 kHz.

* * * * *